United States Patent [19]

Sakata et al.

[11] Patent Number: 4,520,178

[45] Date of Patent: May 28, 1985

[54] PROCESS FOR PRODUCING WATER-INSOLUBLE POLYMERS OF UNIFORM SHAPE FROM GELLED SALTS OF ALGINIC ACID

[75] Inventors: Ko Sakata, Kawasaki; Hirosuke Imai, Yokohama, both of Japan

[73] Assignee: Nippon Oil Co. Ltd., Japan

[21] Appl. No.: 398,589

[22] Filed: Jul. 15, 1982

[30] Foreign Application Priority Data

Jul. 15, 1981 [JP] Japan ................................ 56-109453
Sep. 14, 1981 [JP] Japan ................................ 56-144013

[51] Int. Cl.$^3$ ............................................. C08F 2/20
[52] U.S. Cl. ................................... 526/200; 526/287; 526/306; 526/323.1
[58] Field of Search ........................................ 526/200

[56] References Cited

U.S. PATENT DOCUMENTS 3,953,386  4/1976  Murphy .............................. 526/319
4,238,569  12/1980  Lim .................................... 526/200

OTHER PUBLICATIONS

Condensed Chem. Dict., Reinhold Publ. (NY), 1961, p. 37.

*Primary Examiner*—Christopher A. Henderson
*Attorney, Agent, or Firm*—McGlew and Tuttle

[57] ABSTRACT

A process for producing a water-insoluble polymer of uniform shape having high strength and a desired geometric form is disclosed. This process comprises the steps of dissolving or partially suspending in water (a) a water-soluble salt of alginic acid, (b) a hydrophilic, crosslinkable vinyl monomer having two or more radical-polymerizable vinyl groups per molecule, and (c) optionally a hydrophilic, radical-polymerizable vinyl monomer; bringing the resulting aqueous solution or suspension into contact with an aqueous solution capable of causing gelation of the water-soluble salt of alginic acid and thereby forming an water-insoluble gel of uniform shape; and subjecting the gel to radical polymerization to produce a water-insoluble polymer.

1 Claim, No Drawings

PROCESS FOR PRODUCING WATER-INSOLUBLE POLYMERS OF UNIFORM SHAPE FROM GELLED SALTS OF ALGINIC ACID

BACKGROUND OF THE INVENTION

1. Field of the Invention

This invention relates to a process for producing water-insoluble polymers and, more particularly, to a process for producing a water-insoluble polymer of uniform shape having a desired geometric form.

2. Description of the Prior Art

Conventionally, the production of water-insoluble polymers of uniform size and shape having a desired geometric form from water-soluble, radical-polymerizable monomers and crosslinkable monomers having two or more radical-polymerizable vinyl groups involved several problems concerning formability, variation in shape, controllability of the polymerization reaction, and the like. Thus, its utilization for industrial purposes was very difficult.

In the prior art, suspension polymerization has been used to produce water-insoluble polymers, especially in particulate form, from monomers as described above. According to this process, an aqueous solution of monomers and a surface active agent are added to a medium in which water and the monomers are completely or substantially insoluble. This mixture is vigorously agitated to disperse the aqueous solution of monomers in the form of fine droplets. Then, a polymerization initiator which is easily soluble in the monomers is added to the suspension, whereby polymerization is effected to produce a water-insoluble polymer in particulate form. The particle diameter of the water-insoluble polymer produced by this prior art process depends on the type of medium, monomers, and surface active agent used, the shape of the reactor, and the shape and speed of the agitator. However, this process is normally suitable for the production of a water-insoluble polymer in the form of fine particles having a diameter of 0.1 mm or less. Moreover, the resulting water-insoluble polymer exhibits such a wide particle diameter distribution that it must be sieved if a particulate polymer having a preselected range of particle diameters is desired. The particulate polymer fraction having undesired particle diameters are usually discarded, which makes this process uneconomical. Furthermore, it is extremely difficult to utilize this process in the production of a particulate polymer having a large particle diameter of several millimeters or greater. In this case, it frequently happens that large polymer masses are formed to foul the inner walls of the reactor and thereby force the discontinuance of the operation. Still another disadvantage of suspension polymerization is that it cannot produce a water-insoluble polymer having a geometric form other than the particulate one.

SUMMARY OF THE INVENTION

It is an object of the present invention to provide a novel process for producing a water-insoluble polymer of uniform shape.

It is another object of the present invention to provide a process for producing a hydrophilic, water-insoluble polymer which has a relatively large particle diameter and is suitable for use as a carrier for enzymatically active substances and for other purposes.

It is still another object of the present invention to provide a process for producing a water-insoluble polymer which process facilitates removal of the heat of polymerization and control of the polymerization reaction and causes a bare minimum of fouling of the reactor.

The above and other objects of the present invention are accomplished by a process for producing a water-insoluble polymer of uniform shape which comprises the steps of dissolving or partially suspending in water (a) a water-soluble salt of alginic acid, (b) a hydrophilic, crosslinkable vinyl monomer having two or more radical-polymerizable vinyl groups per molecule, and (c) optionally a hydrophilic, radical-polymerizable vinyl monomer; bringing the resulting aqueous solution or suspension into contact with an aqueous solution capable of causing gelation of the water-soluble salt of alginic acid and thereby forming a water-insoluble gel of uniform shape; and subjecting the gel to radical polymerization to produce a water-insoluble polymer.

DETAILED DESCRIPTION OF THE PREFERRED EMBODIMENTS

Typical examples of the hydrophilic, crosslinkable vinyl monomer having two or more radical-polymerizable vinyl groups which is used in the process of the present invention include acrylamide derivatives such as N,N'-methylenebisacrylamide, N,N'-propylenebisacrylamide, N-acryloylacrylamide, diacrylamido dimethyl ether, 1,2-diacrylamido ethylene glycol, ethyleneurea-bisacrylamide, etc.; unsaturated polyesters prepared by the reaction of an unsaturated polybasic acid such as maleic anhydride, etc. with a polyhydric alcohol; diesters prepared by the reaction of a polyethylene glycol having a molecular weight of 400 to 10,000 and containing less than 30% by weight of propylene oxide units with an unsaturated monocarboxylic acid such as acrylic acid, methacrylic acid, etc.; unsaturated esters prepared by the reaction of an unsaturated polybasic acid such as maleic anhydride, etc. with a polyethylene glycol as described above; unsaturated urethanes prepared by the reaction of a polyethylene glycol as described above with a di- or triisocyanate and an unsaturated monohydroxy compound such as hydroxyethyl methacrylate, etc.; nonionic unsaturated acrylic resins prepared by the reaction of a functional unsaturated compound such as N-methylolacrylamide, etc. with a copolymer of a vinyl monomer or an acrylic monomer containing not less than 50% by weight of a water-soluble nonionic unsaturated compound such as hydroxyethyl methacrylate, acrylamide, etc.; anionic unsaturated acrylic resins prepared by the reaction of a functional unsaturated compound such as glycidyl methacrylate, etc. with a copolymer of a vinyl monomer or an acrylic monomer containing not less than 5% by weight of an unsaturated carboxylic acid such as methacrylic acid, etc.; cationic unsaturated acrylic resins prepared by the reaction of an unsaturated epoxy compound such as glycidyl methacrylate, etc. with a copolymer of a vinyl monomer or an acrylic monomer containing not less than 5% by weight of an unsaturated amino compound such as vinylpyridine, etc.; unsaturated polyvinyl alcohols and unsaturated celluloses prepared by the reaction of a functional unsaturated compound such as N-methylolacrylamide, etc. with a water-soluble synthetic or natural high polymers having hydroxyl groups in its side chains, such as polyvinyl alcohol, hydroxypropyl methyl cellulose, etc.; unsaturated polyamides prepared by the reaction of a functional unsaturated compound such as glycidyl methacrylate, etc. with a water-soluble polyamide such as gelatin, etc.; unsaturated epoxides such as prepared by the addition of an acid anhydride to the hydroxyl groups remaining in an addition product of a polyglycidyl compound, a polycarboxylic acid, and an unsaturated carboxylic acid such as methacrylic acid, etc.; and the like. These radical-polymerizable unsaturated compounds may be used alone or in combination.

Typical examples of the hydrophilic, radical-polymerizable vinyl monomer which is optionally used in the process of the present include unsaturated carboxylic acid salts such as alkali metal (e.g., sodium, potassium, etc.) salts of acrylic acid or methacrylic acid, etc.; acrylic acid and methacrylic acid esters such as hydroxyethyl acrylate, hydroxypropyl acrylate, aminoethyl acrylate, N-methylaminoethyl acrylate, N,N-dimethylaminoethyl acrylate, hydroxyethyl methacrylate, hydroxypropyl methacrylate, aminoethyl methacrylate, N-methylaminoethyl methacrylate, N,N-dimethylaminoethyl methacrylate, etc.; acrylamide derivatives such as acrylamide, methacrylamide, N-methylolacrylamide, N-methylolmethacrylamide, N-methylacrylamide, N,N-dimethylacrylamide, N,N-diethylacrylamide, alkali metal or magnesium salts of 2-acrylamidoethanesulfonic acid or 2-acrylamido-2-methylpropanesulfonic acid, etc.; methyl vinyl ketone; o-, m-, and p-aminostyrenes; alkali metal salts of vinylsulfonic acid or allylsulfonic acid; alkali metal or magnesium salts of styrenesulfonic acid; N-vinylpyrrolidone; acrylic acid or methacrylic acid derivatives of the formula

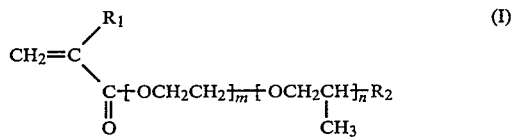

where $R_1$ is a hydrogen atom or a methyl group, $R_2$ is a hydroxyl group, an alkoxy group, an aryloxy group, or a carboxyl group, m is a positive integer of 4 or greater, n is zero or a positive integer, and the ratio of n to m has a value of 0.5 or less; and the like. These monomers may be used alone or in combination.

The preferred acrylic acid or methacrylic acid derivatives which are within the scope of the above formula (I) include:

(1) acrylic or methacrylic monoesters of polyethylene glycol having a polymerization degree of 4 or more;

(2) acrylic or methacrylic monoesters of ethylene oxidepropylene oxide copolymer glycols [poly(oxyethylene-oxypropylene)glycols] having a polymerization degree of 4 or more and a molar oxypropylene/oxyethylene ratio of 0.5 or less;

(3) acrylic or methacrylic monoesters of polyethylene glycol monoethers in which one hydroxyl group of polyethylene glycol having a polymerization degree of 4 or more is replaced by an alkoxy (e.g., methoxy or ethoxy) group having not more than 20 carbon atoms or an aryloxy (e.g., phenoxy) or alkylaryloxy group having not more than 20 carbon atoms;

(4) acrylic or methacrylic monoesters of poly(oxyethylene-oxypropylene)glycol monoethers in which one hydroxyl group of a poly(oxyethylene-oxypropylene)glycol as described in (2) is replaced by an alkoxy (e.g., methoxy or ethoxy) group having not more than 20 carbon atoms or an aryloxy (e.g., phenoxy) or alkylaryloxy group having not more than 20 carbon atoms;

(5) acrylic or methacrylic monoesters of polyethylene glycol monoesters in which one hydroxyl group of polyethylene glycol having a polymerization degree of 4 or more is replaced by an acyloxy (e.g., acetoxy, propionyloxy, or benzoyloxy) group having not more than 20 carbon atoms; and (6) acrylic or methacrylic monoesters of poly(oxyethylene-oxypropylene)glycol monoesters in which one hydroxyl group of a poly(oxyethylene-oxypropylene)glycol as described in (2) is replaced by an acyloxy (e.g., acetoxy, propionyloxy, or benzoyloxy) group having not more than 20 carbon atoms.

In the compounds of formula (I), the ratio of the number of exyethylene units (m) to the number of oxypropylene units (n) must have a value of 0.5 or less so as to facilitate the formation of an alginate gel. No particular limitation is placed on the manner in which the oxyethylene and the oxypropylene units are combined with each other. Thus, the oxyethylene and the oxypropylene units may constitute either a random copolymer or a block copolymer. Moreover, the polyethylene glycol or poly(oxyethylene-oxypropylene)glycol included in these compounds should preferably have a polymerization degree of 4 or more so as to enhance the strength and durability of the resulting water-insoluble polymer.

In producing a water-insoluble polymer according to the present invention, the hydrophilic, crosslinkable vinyl monomer having two or more radical-polymerizable vinyl groups (hereinafter referred to as the crosslinkable vinyl monomer) and the hydrophilic, radical-polymerizable vinyl monomer (hereinafter referred to as the vinyl monomer) are generally used in a ratio ranging from 0.05:0 to 0.05:100 and preferably from 0.1:0 to 0.1:100. As the proportion of the crosslinkable vinyl monomer is decreased, the resulting water-insoluble polymer becomes more likely to swell in water and, when in a water-swollen state (or in the form of the so-called hydrous gel), exhibits higher elasticity and lower tensile strength.

Prior to the polymerization step, the crosslinkable vinyl monomer and optionally the vinyl monomer (hereinafter referred to inclusively as the radical-polymerizable monomers), together with a water-soluble salt of alginic acid, are dissolved in water to form an aqueous alginate solution. However, part of the monomers may be present in a suspended state. The concentration of the radical-polymerizable monomers in the aqueous alginate solution is generally in the range of 0.1 to 50% by weight and preferably 1 to 20% by weight. Nevertheless, the concentration range of 20 to 45% by weight is preferred in order to produce harder polymers. As the concentration of the radical-polymerizable monomers is decreased, the resulting water-insoluble polymer becomes more likely to swell in water and, when in a water-swollen state (or in the form of the so-called hydrous gel), exhibits higher elasticity and lower tensile strength. On the contrary, as the concentration of the radical-polymerizable monomers is increased, the resulting water-insoluble polymer becomes less likely to swell in water and, when in a water-swollen state (or in the form of the so-called hydrous gel), exhibits higher tensile strength with a tendency to embrittlement.

The process of the present invention involves gelation of the water-soluble salt of alginic acid to form a water-insoluble gel (hereinafter referred to as an alginate gel) having the radical-polymerizable monomers contained therein, which is then subjected to polymerization. This polymerization is usually effected by means of a free radical initiator. For this purpose, common water-soluble free radical initiators such as hydrogen peroxide, sodium persulfate, potassium persulfate, ammonium persulfate, and the like are useful. Such a free radical initiator may usually be added to the aqueous alginate solution prior to the formation of an alginate gel. In addition, free radical initiators that are barely soluble or insoluble in water can also be used by dispersing them in the aqueous alginate solution. Thus, similarly to the radical-polymerizable monomers, a free radical initiator may be contained in the alginate gel. Of course, suitable measures (e.g., the maintenance of low temperatures, the use of a free radical initiator that barely decomposes at low temperatures, and the like) should preferably be taken to prevent the free radical initiator from decomposing prior to the succeeding polymerization step. If the polymerization is effected by means of radiation or the like as will be described later, no free radical initiator may be present in the alginate gel. The free radical initiator is generally used in an amount of 0.01 to 10% and preferably 0.1 to 5% based on the total amount of the radical-polymerizable monomers. In addition to the free radical initiator, any desired substances may be added to the aqueous alginate solution, so long as they do not interfere with the formation of an alginate gel and the polymerization reaction.

In carrying out the process of the present invention in order to produce a water-insoluble polymer of uniform shape having a desired geometric form, a water-soluble salt of alginic acid, one or more radical-polymerizable monomers as defined above, and a free radical initiator, if used, are dissolved or partially suspended in water. The resulting aqueous alginate solution is brought into contact with an aqueous solution capable of causing gelation of the water-soluble salt of alginic acid, whereby a gel having a desired geometric form or shape is formed. Thereafter, the radical-polymerizable monomers are polymerized to produce a water-insoluble polymer. Typical examples of the water-soluble salt of alginic acid which is used to form a gel having the radical-polymerizable monomers contained therein include sodium alginate, potassium alginate, ammonium alginate, and the like. Alginic acid is a copolymer of mannuronic acid and guluronic acid obtained from seaweeds. Although its composition may vary according to the place and season of seaweed gathering, any type of alginic acid that forms a gel under the action of a gelling agent for water-soluble salts of alginic acid can be used without regard to composition. The molecular weight of the alginic acid can range from 1,000 to 1,000,000. The concentration of the water-soluble salt of alginic acid in the aqueous alginate solution used to form an alginate gel is generally in the range of 0.1 to 20% by weight and preferably 0.5 to 10% by weight. If the alginate concentration is lower than the aforesaid range, the resulting alginate gel is too low in strength to form into a desired shape and the radical-polymerizable monomers tends to escape from the gel. On the other hand, if the alginate concentration is higher than the aforesaid range, the resulting alginate gel has high strength, but the aqueous alginate solution is too high in viscosity to handle or to form into a gel having a desired shape, and this is also disadvantageous from an economical point of view. Preferably, any dissolved oxygen is removed from the aqueous alginate solution containing the radical-polymerizable monomers so that the polymerization reaction may proceed smoothly in the succeeding polymerization step. This can be done, for example, by introducing thereinto an inert gas such as nitrogen gas.

The aqueous solution capable of causing gelation of the aqueous alginate solution (hereinafter referred to as the gelling agent solution) comprises, for example, an acidic aqueous solution having a pH of 7 or lower and containing divalent or higher polyvalent ions of a metal other than magnesium and mercury. Typical examples of the substance used to acidify the solution include inorganic acids such as hydrochloric acid, sulfuric acid, nitric acid, etc. and organic acids such as formic acid, acetic acid, etc. Typical examples of the polyvalent metal ions include ions of metals such as Ca, Fe, Mn, Co, Ni, Zn, Cd, Sr, Cu, Pb, Ba, etc. As will be described later, an acidic aqueous solution having a pH of 4 to 7 is preferably used in cases where it is intended to entrap living microorganic cells in the alginate gel.

In order to form an alginate gel containing the radical-polymerizable monomers and occasionally the free radical initiator, the aqueous alginate solution containing the radical-polymerizable monomers and occasionally the free radical initiator is brought into contact with the above-described gelling agent solution.

The geometric form or shape of the alginate gel so formed can be changed by varying the method of contact. For example, spherical alginate gel particles having a high degree of sphericity and a very limited diameter distribution can be formed by adding the aqueous alginate solution containing the radical-polymerizable monomers dropwise to the gelling agent solution or by spouting the former into the latter. The diameter of the resulting spherical gel particles depends on the viscosity of the aqueous alginate solution, the shape of the nozzle used for the addition or sprouting of the aqueous alginate solution, and the like. Moreover, where the aqueous alginate solution containing the radical-polymerizable monomers is injected into the gelling agent solution, the shape of the resulting alginate gel can be changed by modifying the shape of the injection nozzle. Furthermore, an alginate gel having a desired shape can be very easily formed by pouring the aqueous alginate solution into a mold and then soaking the mold in the gelling agent solution with part of the mold left open. Thus, the gelling agent solution enters the cavity of the mold by the opening and comes into contact with the aqueous alginate solution to cause gelation of its surface layer. Subsequently, the gelling agent solution penetrates into the aqueous alginate solution until its entire body within the mold undergoes gelation. Alternatively, an alginate gel in sheet form can be obtained by spreading the aqueous alginate solution in a shallow dish and then pouring the gelling agent solution on it gently. The resulting gel sheet can further be subjected to stamping. Alternatively, an alginate gel having a desired shape can be formed by mixing the aqueous alginate solution with the gelling agent solution in a high-speed blender and immediately pouring the resulting blend into a mold. In this gelling procedure, a gelation retarder such as an alkali metal salt of phosphoric acid, an alkali metal salt of citric acid, or the like may be added to the blend. After being formed according to one of the above-described procedures, the alginate gel can further be cut into a desired shape.

The above-described step of forming an alginate gel must be carried out at a temperature lower than that at which the free radical initiator begins to decompose and thereby initiates the polymerization reaction. Thus, this step is generally carried out at a temperature ranging from 0° C. to 100° C. Moreover, this step should preferably be carried out in an atmosphere of an inert gas (e.g., nitrogen gas) so that the polymerization reaction may proceed smoothly in the succeeding polymerization step.

The resulting alginate gel containing the radical-polymerizable monomers is then subjected to polymerization. This polymerization step is preferably carried out by placing the alginate gel in a solvent (e.g., water, alcohol, a hydrocarbon solvent, or the like) that does not interfere with radical polymerization and then removing any dissolved oxygen from the reaction system. However, it is also possible to carry out the polymerization step without using a solvent and in a stream of an inert gas freed of oxygen. The polymerization temperature needs only to be equal to or higher than the decomposition temperature of the free radical initiator, though it may vary according to the type of free radical initiator used. Where it is desired to carry out the polymerization step at low temperatures, a solution containing a reagent (e.g., tetramethylethylenediamine for hydrogen peroxide, ferrous ions for potassium persulfate, or the like) that accelerates the decomposition of the free radical initiator may be brought into contact with the alginate gel for the purpose of lowering the decomposition temperature of the free radical initiator. Where no free radical initiator is present in the alginate gel containing the radical-polymerizable monomers, radical polymerization can be effected by exposing the alginate gel to radiation.

The steps of forming an alginate gel from the aqueous alginate solution and subjecting the gel to polymerization may be carried out separately or successively. In the latter case, the aqueous alginate solution containing the radical-polymerizable monomers is brought into contact with the gelling agent solution kept at a temperature higher than the decomposition temperature of the free radical initiator. Thus, simultaneously with the formation of an alginate gel, the polymerization reaction is initiated to produce a water-insoluble polymer having a desired shape.

The water-insoluble polymer so produced contains the alginate which was used for the formation of an alginate gel. If this alginate is unnecessary for the intended use of the polymer or has an adverse effect thereon, it may be removed from the water-insoluble polymer. Substances that can chelate the polyvalent metal ions to form water-soluble metal ions are useful for the purpose of removing the alginate, and typical examples thereof include sodium or potassium salts of ethylenediaminetetraacetic acid, alkali metal salts of phosphoric acid, hydroxides and carbonates of alkali metals, and the like. In order to remove the alginate, the water-insoluble polymer resulting from the polymerization step may be soaked in or washed with an aqueous solution of such a substance at a temperature of 0° to 100° C. Alternatively, the alginate can also be removed by washing the water-insoluble polymer, for a sufficiently long period of time, with water containing no polyvalent metal ions and having a pH of 7 or higher.

The water-insoluble polymer produced by the process of the present invention has an adequate degree of hydrophilicity in spite of its insolubility in water. In fact, the water-insoluble polymer resulting from the polymerization step is in a water-swollen state. Depending on its intended use, this water-insoluble polymer may be used directly or after being thoroughly washed with water. Furthermore, the water-insoluble polymer may be dried or freed of water prior to use.

The water-insoluble polymers produced by the process of the present invention have the advantage of being uniform in shape, and this feature can be fully utilized when they are used as carriers for enzymatically active substances. Especially by adding a desired microorganism to the aqueous alginate solution prior to the formation of an alginate gel, a water-insoluble polymer of uniform shape which not only has the microorganism entrapped therein but also has high strength and serves for a long time can be produced and effectively utilized in enzymatic processes using that microorganism. Moreover, when in a dried state, the water-insoluble polymers of the present invention exhibit such a high degree of absorptivity that they can be used as absorbent polymers. Thus, their uniformity in shape can be fully utilized in such applications as soil conditioners, cold insulators, sanitary materials (e.g., paper diapers, sanitary napkins, etc.), and the like.

In order to further illustrate the present invention, the following examples are given. However, these examples are not to be construed to limit the scope of the invention.

EXAMPLE 1

An aqueous alginate solution was prepared by dissolving 15 g of acrylamide, 1 g of N,N'-methylenebisacrylamide, and 2 g of sodium alginate (Duck Algin NSPM, a product of Kamogawa Kasei Co.) in water to make to a total amount of 100 g, and adding thereto 1 ml of a 1% (w/w) aqueous solution of hydrogen peroxide. Through this aqueous alginate solution was bubbled nitrogen gas. While a solution of 1 g of ferrous sulfate and 6 g of calcium chloride in 300 ml of water was kept at 20° C., the above aqueous alginate solution was added dropwise thereto in a stream of nitrogen gas. The resulting suspension containing spherical gel particles was then subjected to polymerization by allowing it to stand at 50° C. for 1 hour in a stream of nitrogen gas. Thus, a water-insoluble copolymer was produced in the form of spherical particles having a uniform diameter of 3 mm.

EXAMPLE 2

A 20 g portion of the water-insoluble copolymer particles produced in Example 1 was placed in a 1-liter vessel, and 500 ml of a 2N aqueous solution of sodium hydroxide was added thereto. The resulting mixture was stirred at 20° C. for 5 hours. As a result, there were obtained water-insoluble copolymer particles which were substantially free of alginate and in the form of spherules having a uniform diameter of 4 mm.

EXAMPLE 3

An aqueous alginate solution was prepared by dissolving 10 g of 2-acrylamido-2-methylpropanesulfonic acid and 1 g of N,N'-methylenebisacrylamide in water, adjusting the resulting solution to pH 7 with sodium hydroxide, diluting it with water to a total amount of 98 g, dissolving therein 2 g of sodium alginate (Duck Algin NSPM, a product of Kamogawa Kasei Co.), and adding thereto 1 ml of a 5% (w/w) aqueous solution of ammonium persulfate. Through this aqueous solution was bubbled nitrogen gas to expel any dissolved oxygen. While a solution of 1 g of tetramethylethylenediamine and 6 g of calcium chloride in 300 g of water was kept at room temperature, the above aqueous alginate solution was added dropwise thereto in a stream of nitrogen gas. The resulting suspension containing spherical gel particles was then subjected to polymerization by allowing it to stand at 80° C. for 1 hour in a stream of nitrogen gas. Thus, a water-insoluble copolymer was produced in the form of spherical particles. A 20 g portion of the particles was packed into a column having an internal volume of 60 ml, and a 1N aqueous solution of sodium hydroxide was passed therethrough for 10 hours at a rate of 20 ml/hr. As a result, there were obtained water-insoluble copolymer particles which were substantially free of alginate and in the form of spherical particles having a uniform diameter of 5 mm.

A 20 g portion of the particles so produced was packed into a tubular reactor having an internal volume of 40 ml and then sterilized by treatment with steam at 120° C. for 15 minutes. One hundred milliliters of a culture medium for yeast (containing 10% of glucose, 0.15% of yeast extract, 0.25% of ammonium chloride, 0.1% of sodium chloride, 0.55% of dipotassium phosphate, 0.01% of magnesium sulfate, 0.001% of calcium chloride, and 0.3% of citric acid) was inoculated with J.B.A. (Japan Brewers' Association) No. 6 yeast to form a yeast cell suspension. This was done by dipping a yeast-loaded platinum loop into the medium and repeating this operation 50 times. While the above reactor was kept at 30° C., the yeast cell suspension was passed thereto for 24 hours at a rate of 4 ml/hr. Thereafter, the yeast cell suspension was replaced by a culture medium as described in Example 7, which was passed through the reactor with its temperature kept at 30° C. After 3 days, the effluent emerging from the outlet of the reactor had an ethanol concentration of 4% by weight.

EXAMPLE 4

An aqueous alginate solution was prepared by dissolving 9 g of 2-acrylamido-2-methylpropanesulfonic acid, 1 g of 2-hydroxyethyl methacrylate, and 1 g of N,N'-methylenebisacrylamide in water, adjusting the resulting solution to pH 7 with sodium hydroxide, diluting it with water to a total amount of 98 g, dissolving therein 2 g of sodium alginate (Duck Algin NSPM, a product of Kamogawa Kasei Co.), and adding thereto 1 ml of a 1% (w/w) aqueous solution of hydrogen peroxide. Through this aqueous alginate solution was bubbled nitrogen gas to expel any dissolved oxygen. On the other hand, a solution of 1 g of ferrous sulfate in 300 ml of water was adjusted to pH 1 with concentrated sulfuric acid. Through this ferrous sulfate solution was bubbled nitrogen gas to expel any dissolved oxygen. While the ferrous sulfate solution was kept at 20° C., the above aqueous alginate solution was added dropwise thereto in a stream of nitrogen gas. The resulting suspension containing spherical gel particles of uniform diameter was subjected to polymerization by allowing it to stand at 50° C. for 3 hours in a stream of nitrogen gas. Thus, a water-insoluble copolymer was produced in the form of particles. A 20 g portion of the particles was worked up in the same manner as in Example 2. As a result, there were obtained water-insoluble copolymer particles which were substantially free of alginate and in the form of spherules having a diameter of 3 mm.

EXAMPLE 5

An aqueous alginate solution containing vinyl monomers was prepared in the same manner as in Example 3, and a ferrous chloride solution was prepared in the same manner as in Example 4. While the ferrous sulfate solution was kept at 20° C., the aqueous alginate solution was injected thereinto in a stream of nitrogen gas by means of a syringe. The resulting suspension containing spherical gel particles was then subjected to polymerization by allowing it to stand at 50° C. for 3 hours in a stream of nitrogen gas. Thus, a water-insoluble copolymer was produced in the form of spherical particles having a uniform diameter of 8 mm. A 20 g portion of the water-insoluble copolymer particles so produced was worked up in the same manner as in Example 2. As a result, there were obtained water-insoluble copolymer particles which were substantially free of alginate and in the form of spherules having a uniform diameter of 10 mm.

EXAMPLE 6

One hundred grams of a 5% aqueous solution of sodium alginate (Kelgin MV, a product of Sansho Co.) was sterilized by heating at 120° C. for 10 minutes. To this sodium alginate solution were added 1 g of polyethylene glycol dimethacrylate (having a molecular weight of 1000), 5 g of 2-acrylamido-2-methylpropanesulfonic acid sodium salt, and 0.05 g of ammonium persulfate. Then, sterilized nitrogen gas was bubbled through the sodium alginate solution, which was inoculated with J.B.A. No. 6 yeast by dipping a yeast-loaded platinum loop thereinto and repeating this operation 50 times. Separately, 300 ml of a 5% aqueous solution of calcium chloride was placed in a 500-ml separable flask and heated at 120° C. for 10 minutes. After the addition of 1 g of tetramethylethylenediamine, sterilized nitrogen gas was bubbled through the calcium chloride solution. While the calcium chloride solution was kept at 20° C. with gentle stirring, the above sodium alginate solution was added dropwise thereto by means of a sterilized microtube pump (this operation was carried out in a stream of sterilized nitrogen gas). Thus, gel particles having a diameter of approximately 3 mm were formed. The resulting gel suspension was subjected to polymerization by allowing it to stand at 40° C. for 4 hours. The particles so produced were aseptically packed into a jacketed glass column having a diameter of 2 cm and a height of 10 cm. Then, a nutrient medium for yeast (containing 10% of glucose, 0.15% of yeast extract, 0.25% of ammonium chloride, 0.1% of sodium chloride, 0.55% of dipotassium phosphate, 0.01% of magnesium sulfate, 0.001% of calcium chloride, and 0.3% of citric acid) was passed therethrough from the bottom at a rate of 8 ml/hr, the internal temperature of the column being kept at 30° C. One week after commencement of the passage of the nutrient medium, the particles were removed from the column. On microscopic examination of cross sections of some particles, a large number of yeast colonies were found in the vicinity of their surfaces. Then, the particles were introduced into a 2% aqueous solution of ethylenediaminetetraacetic acid tetrasodium salt, but they remained perfectly spherical even after a day. This clearly indicates that these particles do not comprise an alginate gel.

EXAMPLE 7

A solution of 2 g of sodium alginate (Duck Algin NSPM, a product of Kamogawa Kasei Co.) in 87 g of water was sterilized by heating at 120° C. for 10 minutes. To this aqueous alginate solution were added 9 g of 2-acrylamido-2-methylpropanesulfonic acid sadium salt, 1 g of N,N'-methylenebisacrylamide, and 1 ml of a 5% (w/w) aqueous solution of ammonium persulfate. The resulting solution was inoculated with J.B.A. No. 6 yeast to form a yeast cell suspension. This was done by dipping a yeast-loaded platinum loop into the solution and repeating this operation 10 times. On the other hand, a 2% (w/w) aqueous solution of calcium chloride was sterilized by heating at 120° C. for 10 minutes. After the addition of 1 g of tetramethylethylenediamine, sterilized nitrogen gas was bubbled through the calcium chloride solution. The above yeast cell suspension was added dropwise to the calcium chloride solution by means of a syringe. Thus, spherical alginate gel particles having an average diameter of 3 mm were formed. The resulting alginate gel suspension was subjected to polymerization by allowing it to stand at 40° C., with gentle stirring, in a stream of sterilized nitrogen gas. Thus, a water-insoluble copolymer containing the alginate gel was produced in the form of spherical particles having a diameter of 3 mm. A 20 g portion of the particles was packed into a jacketed glass column having an internal volume of 40 ml. While this column was kept at 30° C., a culture medium (containing 10% of glucose, 0.15% of yeast extract, 0.25% of ammonium chloride, 0.1% of sodium chloride, 0.55% of dipotassium phosphate, 0.025% of magnesium sulfate heptahydrate, 0.001% of calcium chloride, and 0.3% of citric acid and adjusted to pH 5) was passed therethrough from the bottom. Four days after commencement of the passage of the culture medium, the effluent emerging from the outlet of the column had an ethanol concentration of 5% by weight.

EXAMPLE 8

An aqueous alginate solution was prepared by dissolving 10 g of polyethylene glycol dimethacrylate (NK Ester 14G, a product of Shin-Nakamura Kagaku Co.) and 1.5 g of sodium alginate (Duck Algin NSPM, a product of Kamogawa Kasei Co.) in water to make a total amount of 100 g, and adding thereto 1 ml of a 1% (w/w) aqueous solution of hydrogen peroxide. Through this aqueous alginate solution was bubbled nitrogen gas. While a solution of 1 g of ferrous sulfate and 6 g of calcium chloride in 300 ml of water was kept at 20° C., the above aqueous alginate solution was added dropwise thereto in stream of nitrogen gas. The resulting suspension containing spherical gel particles was then subjected to polymerization by allowing it to stand at 50° C. for 1 hour in a stream of nitrogen gas. Thus, a water-insoluble copolymer was produced in the form of spherical particles having a uniform diameter of 3 mm.

EXAMPLE 9

A 20 g portion of the water-insoluble copolymer particles produced in Example 8 was placed in a 1-liter vessel, and 500 ml of a 2N aqueous solution of sodium hydroxide was added thereto. The resulting mixture was stirred at 20° C. for 5 hours. As a result, there were obtained water-insoluble copolymer particles which were substantially free of alginate and in the form of spherules having a uniform diameter of 4 mm.

EXAMPLE 10

An aqueous alginate solution was prepared by dissolving 10 g of polyethylene glycol dimethacrylate (containing approximately 10% of oxypropylene units and having a molecular weight of 1100) and 1 g of sodium alginate (Duck Algin NSPM, a product of Kamogawa Kasei Co.) in water to make a total amount of 100 g, and adding thereto 1 ml of a 5% (w/w) aqueous solution of potassium persulfate. Through this aqueous alginate solution was bubbled nitrogen gas. While a solution of 1 ml of N,N,N',N'-tetramethylethylenediamine and 6 g of calcium chloride in 300 ml of water was kept at 20° C., the above aqueous alginate solution was injected thereinto through a nozzle in a stream of nitrogen gas. The resulting suspension containing spherical gel particles was then subjected to polymerization by allowing it to stand at 50° C. for 1 hour in a stream of nitrogen gas. Thus, a water-insoluble copolymer was produced in the form of spherical particles having an average diameter of 0.3 mm.

EXAMPLE 11

An aqueous alginate solution was prepared by dissolving 10 g of polyethylene glycol dimethacrylate (NK Ester 14 G, a product of Shin-Nakamura Kagaku Co.) and 1 g of sodium alginate (Kelgin MV, a product of Sansho Co.) in water to make a total amount of 100 g. Through this aqueous alginate solution was bubbled nitrogen gas. In a stream of nitrogen gas, the above aqueous alginate solution was added dropwise to a solution of 6 g of calcium chloride in 300 ml of water. Through the resulting suspension containing spherical gel particles was bubbled nitrogen gas. After the addition of 4 ml of a 5% (w/w) aqueous solution of potassium persulfate and 4 ml of N,N,N',N'-tetramethylethylenediamine, this suspension was subjected to polymerization by allowing it to stand at 50° C. for 1 hour. Thus, a water-insoluble copolymer was produced in the form of spherical particles having an average diameter of 1.7 mm.

EXAMPLE 12

A solution of 2 g of sodium alginate (Duck Algin NSPM, a product of Kamogawa Kagaku Co.) in 93 g of water was sterilized by heating at 120° C. for 15 minutes. To this aqueous alginate solution were added 10 g of polyethylene glycol (600) dimethacrylate (NK Ester 14G, a product of Shin-Nakamura Kagaku Co.) and then 1.2 g of potassium persulfate. This mixture was made into a homogeneous solution, through which sterilized nitrogen gas was bubbled.

A nutrient medium (containing 0.5% of glucose, 1.25% of yeast extract, 1.0% of peptone, 0.5% of meat extract, and 0.5% of sodium chloride and adjusted to pH 7.0) was inoculated with Serratia marcescens [R.I.M.I. (Research Institute of Microorganic Industry) No. 390] and shaken at 30° C. for 16 hours. Five milliliters of this culture was added to the above aqueous alginate solution. Separately, a 5% aqueous solution of calcium chloride was prepared and sterilized by heating at 120° C. for 15 minutes. While this calcium chloride solution was kept at 20° C., the aqueous alginate solution containing microorganic cells was added dropwise thereto in a stream of sterilized nitrogen gas. Thus, gel particles having a diameter of 1.8 mm were formed. The resulting gel suspension was then subjected to polymerization by allowing it to stand at 40° C. for 4 hours. The particles so produced were aseptically packed into a jacketed glass column having a diameter of 2 cm and a height of 10 cm. Then, a nutrient medium as described above was passed therethrough from the bottom at a rate of 8 ml/hr, the internal temperature of the column being kept at 30° C. After 60 hours, the effluent emerging from the outlet of the column had an isoleucine concentration of 2.4 mg/ml.

What is claimed is:

1. A process for producing a water-insoluble polymer of uniform shape, which comprises the steps of
(i) dissolving or partially suspending in water
  (a) no more than 20% by weight, based on the aqueous solution or suspension, of a water-soluble salt of alginic acid,
  (b) a hydrophilic, crosslinkable vinyl monomer having two or more radical-polymerizable vinyl groups per molecule, and
  (c) a hydrophilic, radical-polymerizable vinyl monomer, the combined concentration of (b) and (c) not exceeding 50% by weight, based on the aqueous solution or suspension;
(ii) contacting the resulting aqueous solution or suspension with an aqueous gelling solution to gel the salt of alginic acid and thus form a water-insoluble gel of uniform shape; and
(iii) subjecting the gel to radical polymerization to produce a water-insoluble polymer.

* * * * *